(12) United States Patent
Ghosh et al.

(10) Patent No.: US 7,713,734 B2
(45) Date of Patent: May 11, 2010

(54) DEVICE FOR CULTURING AND TRANSPORTING CELLS

(75) Inventors: Deepa Ghosh, Maharashtra (IN); Sudheer Shenoy, Maharashtra (IN)

(73) Assignee: Reliance Life Sciences Pvt Ltd, Rabale, Navi Mumbai (IN)

( * ) Notice: Subject to any disclaimer, the term of this patent is extended or adjusted under 35 U.S.C. 154(b) by 1085 days.

(21) Appl. No.: 11/385,017

(22) Filed: Mar. 20, 2006

(65) Prior Publication Data

US 2007/0166819 A1    Jul. 19, 2007

(51) Int. Cl.
*C12M 1/22* (2006.01)
*C12M 3/00* (2006.01)

(52) U.S. Cl. .............. 435/305.4; 435/288.3; 435/297.1; 435/297.5; 435/305.1

(58) Field of Classification Search .............. 435/285.2, 435/288.3, 297.1–297.5, 305.1–305.4
See application file for complete search history.

(56) References Cited

U.S. PATENT DOCUMENTS

| | | | |
|---|---|---|---|
| 3,450,598 A | 6/1969 | Welsh | |
| 3,821,087 A | 6/1974 | Knazek | |
| 3,883,393 A | 5/1975 | Knazek | |
| 3,997,396 A | 12/1976 | Delente | |
| 4,184,822 A | 1/1980 | Schwabauer | |
| 4,200,689 A | 4/1980 | Knazek | |
| 4,206,015 A | 6/1980 | Knazek | |
| 4,220,725 A | 9/1980 | Knazek | |
| 4,334,028 A | 6/1982 | Carver | |
| 4,391,912 A | 7/1983 | Yoshida | |
| 4,400,258 A * | 8/1983 | Hans-Jurgen et al. | 204/415 |
| 4,608,342 A * | 8/1986 | Nees | 435/401 |
| 4,851,351 A | 7/1989 | Akamine | |
| 4,962,033 A | 10/1990 | Serkes | |
| 5,010,013 A | 4/1991 | Serkes | |
| 5,190,878 A * | 3/1993 | Wilhelm | 435/297.2 |
| 5,366,893 A * | 11/1994 | Stevens et al. | 435/297.5 |
| 5,398,837 A | 3/1995 | Degrassi | |
| 5,409,832 A * | 4/1995 | Pocock | 435/288.3 |
| 5,527,705 A | 6/1996 | Mussi | |
| 5,652,142 A * | 7/1997 | Barker et al. | 435/297.1 |
| 5,693,332 A | 12/1997 | Hansbrough | |
| 5,766,937 A * | 6/1998 | Lahm et al. | 435/297.5 |
| 5,795,775 A * | 8/1998 | Lahm et al. | 435/297.5 |
| 5,863,792 A * | 1/1999 | Tyndorf et al. | 435/297.5 |
| 2003/0208266 A1 | 11/2003 | Tsai | |

* cited by examiner

*Primary Examiner*—Walter D Griffin
*Assistant Examiner*—Shanta G Doe
(74) *Attorney, Agent, or Firm*—Vinson & Elkins LLP (57) ABSTRACT

A disposable device is provided for culturing and/or packaging and transporting ready-to-use viable cells cultured on membranes, gels or micro porous substrata. The device includes a housing base defining an interior for culturing cells. The membrane to be used for culturing the cells is placed inside the housing base and fixed with a ring. The base is closed by a lid, which is designed to protect the underlying cells during transport as well as minimize the volume of media used during culture, as well as transport. Media leakage is prevented by the silicon gasket as well as the snaps provided in the device.

23 Claims, 8 Drawing Sheets

DEVICE FOR CULTURING AND TRANSPORTING CELLS

CROSS-REFERENCES TO RELATED APPLICATIONS

Not applicable.

STATEMENT REGARDING FEDERALLY SPONSORED RESEARCHED OR DEVELOPMENT

Not applicable.

REFERECE TO A "MICROFICHE APPENDIX"

Not applicable.

BACKGROUND OF THE INVENTION

1. Field of the Invention

This invention relates to the field of biological cell culture equipment and more particularly to devices for culturing and transport of cells. The present invention involves devices that can be used to support a film, membrane or sponge for the purpose of isolation, expansion, transportation and/or transplantation of cells.

2. Description of Related Art

Cell culture is a process of growing and maintaining cells under laboratory conditions. This process involves isolating the cells from animals or plants, and growing and maintaining the living cells in laboratory devices using artificial culture media to support their basic biological functions. Cell cultures are derived from either primary tissue explants or from cell suspensions. Depending on the nature of the isolated cells, the cells can be either of the adherent or the suspension type. Various methods are known in the art for growing cells in both large scale and small scale cultures.

Various cell culture devices are commercially available in several shapes and designs, the most widely used conventional forms being culture flasks and dishes. The flasks are provided with caps, while the dishes are available as individual or multi well dishes, and are provided with lids.

Typically available individual culture dishes include a base for containing the cultures and a lid to cover the container. The primary purpose of the culture dish is to support cell growth. For practicing cell culture, cells isolated from the tissues are seeded in the culture device along with the nutrient media to nourish the cells, followed by incubation in a controlled. environment. A transparent material like polystyrene is preferred in the manufacture of cell culture dishes to enable visualization of the cultured cells under a microscope.

Conventional cell culture dishes require protection against microbial contamination for successful cell growth, since contamination is one of the principal challenges to successful cell and tissue culturing techniques. Culture dish contamination is typically minimized by using sterilized dishes. The lid serves as a barrier to airborne microbes and prevents evaporation of the media. Conventional cell culture plate lids, however, serve only as a barrier to microbial contamination and do not provide a tight seal that prevents spillage of the contents during transport of the cell cultures.

Specific cells are cultured in dishes under sterile conditions to a desired state of growth for specialized purposes as in the case of medical, scientific or industrial requirements. Following growth, however, these cells have to be removed from their growth environment and shipped to the required end users. For transport of the cultured cells, the cells have to be separated from the dish using enzymes like trypsin, placed within cryoprotectants and shipped under liquid nitrogen. After the cells arrive, they must be re-cultured to maintain their viability. In addition to the time and resources required in re-culturing the cells, this necessity results in significant delays while waiting for the cells to grow to the desired state. The hostile transport conditions also result in considerable loss in viability of cells as well as high shipping costs.

Currently, cell based therapies are being practiced at least in the areas of skin, cornea, cartilage, etc., and the use of cultured cells for medical applications is growing rapidly. There is a growing need, therefore, for an efficient method of delivering cells to the site of transplantation. Cells for use in transplantation therapies can be grown either as monolayers on suitable membranes as described in U.S. Pat. No. 5,693,332 and/or as differentiated into multilayers as published in U.S. Publ. No. 2003/0208266A1 (each incorporated herein by reference in their entireties) before transplantation, or the cells can be cultured on foams or sponges, which can then be transplanted. The important factors involved in membrane-based cell delivery systems include, attachment, viability, cell density, and control over differentiation. The delicate relationship between the cell layers and the membrane can be disturbed during shipment due to movement shear, tear and/or other mechanical damage to the individual cells and their contacts with each other, thus destroying confluence of the monolayer and rendering the cells useless. Although the cells can be cultured on membranes in culture dishes, their transport in the same dishes is not feasible.

Culture flasks were developed to address the problem of contamination in cell culture dishes. Conventional flasks typically have a culture chamber, a small tubular opening located at one end of the flask, and a corresponding closure. The principal designs for various culture flasks are described in U.S. Pat. Nos. 4,334,028, 4,851,351 and 5,398,837 (each incorporated herein by reference in their entirety). As these culture flasks require a relatively large amount of expensive media in order to be filled completely, they are not cost effective. Conventional flasks are also not suitable for the growth of cells for transplantation, as a film or membrane cannot be placed inside the flask to grow cells for transplantation.

Further to dishes and flasks, roller bottles have also been developed for cell culture. Roller bottles offer a larger surface area for cell attachment and growth. Due to the presence of high shear forces associated with these roller bottles, however, this technology is suitable only for those cells that are capable of remaining adhered to the wall of the roller bottle. Also the maintenance of cell cultures in roller bottles for longer periods poses a challenge due to a constant high shear force environment and possible contamination. U.S. Pat. No. 3,450,598 (incorporated herein by reference in its entirety) involves attaching and growing cells on the interior surface of plastic or glass roller tubes and bottles. Other aspects of roller bottle technology are described in U.S. Pat. Nos. 5,527,705 and 4,962,033 (each incorporated herein by reference in their entirety). Further improvements to roller bottles with increased surface areas for cell attachment are described in U.S. Pat. No. 5,010,013 (incorporated herein by reference in its entirety), wherein corrugated channels are added to the interior surface area of the roller bottle. Roller bottles still suffer various inefficiencies, however, including not providing sufficient aeration to the cells, thus diminishing their viability.

More recently, the use of hollow fibers or capillaries has been disclosed as a support matrix for the propagation of cells. This technology is described in U.S. Pat. Nos. 3,821,087, 3,883,393, 3,997,396, 4,184,822, 4,200,689, 4,206,015, 4,220,725, and 4,391,912 (each incorporated herein by reference in their entirety), wherein various apparatus and methods for the in vitro growth of cells on semi-permeable tubular membranes or capillaries are disclosed. The cells are initially allowed to settle onto the surfaces of the capillary walls in a nutrient medium. The nutrients diffuse from the perfusing medium through the capillary walls and are utilized by the cells. Cell products diffuse from the cells through the capillary walls and into the perfusate, from which cell products may be recovered. Unfortunately, nutrient media flow through the hollow capillaries prevents complete penetration of the capillary bundle by the cells and the resultant undesirable gradient of the medium flow leads to incomplete utilization of the available capillary surface for cell attachment. This results in the cells becoming unevenly distributed along the surface. Furthermore, these devices require high media circulation rates to supply adequate oxygen to the cells, and these devices have the additional disadvantages of being mechanically complex, difficult to assemble, and unduly large.

Considering the state of the art, there is a continuing need for an efficient and economical device for culturing, expansion and transport of cell cultures, and it would be beneficial to provide a device suitable for culturing and transporting cell monolayers attached to permeable membranes that are ready to use upon delivery.

BRIEF SUMMARY OF THE INVENTION

The present disclosure addresses at least some of the problems described above by providing a compact, portable, commercially viable and easy-to-use device for culturing and transporting of cells in a single device. In preferred embodiments, a user can load a membrane of choice into the device for culturing cells and then use the device to transport the cultured cells to a recipient's location, for example to transplant the membrane to repair or regenerate damaged tissue. The devices of the present disclosure thus provide the ability to culture cells either in a mono-layer or in multilayers, and transport the cells in the same device while maintaining their viability sufficiently that the culture can be removed from the device and used as a transplant, implant, or graft after transport.

The present disclosure provides a device for cell culture that has various advantages over known cell culture devices. These advantages include but are not limited to the device being disposable, sterile and safe for culturing and transporting adherent cells cultured on a membrane in which the membrane remains taut and undamaged during transport. Preferred embodiments of the disclosure also provide for handling and transportation of cells free from microbial contamination and in a low volume of media. Preferred embodiments also include devices fabricated with a safe, non-toxic, non pyrogenic and transparent material, preferably polyethylene, polystyrene, polyethylene terephthalate, or polycarbonate, thus allowing the cells to be observed under a microscope.

In an exemplary embodiment, a device of the present disclosure includes a base structure, or base plate and a cover, cap, or lid. In this example, the base plate provides exterior, side walls, configured to rest on their bottom surfaces on a flat surface. The walls may also terminate at the bottom in a rim that is bonded, affixed or continuous with the bottom edges of the side walls, and provides one or more co-planar contact points to rest on a flat surface and to hold the base in an upright and stable position. The side walls of the base are preferably connected to each other around the perimeter of the base and by a flat or planar top member resting on the tops of the side walls, but with the bottom of the base being open. The bottoms of the side walls can also provide at least part of the mechanism for sealing the device for transport. In preferred embodiments, each of the side walls of the base includes a notch to accept a snap closure that is provided on the lid or cover. The mechanism may be configured in various positions and in certain embodiments, a notch is provided near the center line in the bottom of each base plate side wall and in areas where the side wall does not terminate at the bottom in a rim. It is understood that the side walls and top of the base plate are often molded from a single sheet or piece of material, although the side walls and top can be formed separately and joined, for example, by an adhesive, chemical or thermal process. The rim also may be molded with the side walls, or it may be a separate piece and of separate material such as a softer, rubber like material, or of a thicker width for providing a more stable platform for the device.

The planar top of the base plate provides a well, housing device or chamber, comprising side walls and a bottom, preferably centered in the top plate surface, wherein the chamber extends down from the top surface and is spaced inwardly from the base plate side walls. The chamber or well is sized and configured to accept the membrane for cell culture and to hold the cell culture media. Although the well may be of any two-dimensional shape when viewed from above, the shape is preferably round or it may be square or rectangular as needed to best accommodate the shape of the desired culture membrane. The base plate also includes a groove, disposed between the planar top and the chamber side walls, such that the top or rim of the side walls of the chamber are separated from the planar top of the base plate by a continuous groove around the circumference or perimeter of the well. The housing device or well extends downward into the base to the appropriate depth to function as a cell culture chamber and can extend as far as the plane of the bottom of the base plate side walls.

In preferred embodiments of the disclosure, a gasket, O-ring, or other resilient, or stiff structural member is provided that fits snugly into the base of the well or chamber in the base plate. When the well is round, the gasket is a ring shaped member such as an O-ring. The ring may be made of various materials that resiliently hold their shape if deformed, such as, for example, rubber. The ring functions to hold a cell growth membrane on the bottom of the well during use to prevent the membrane from floating or wrinkling in the liquid cell culture media.

In another embodiment of the present disclosure, the cell culture device includes a base structure, cover, and a ring structure. Preferably the base structure comprises a planar top member and one or more side walls, each with an upper and lower edge, wherein the one or more side walls adjoin the planar top member at the upper edge. In addition, the base structure preferably comprises a well formed in the top member, a groove surrounding the well between the planar portion of the top member and the well, and one or more notches in the lower edge of the one or more side walls configured to receive a latching mechanism. The cover of the device preferably comprises a planar top member having an upper and a lower surface, and one or more side walls, each with an upper and lower edge, wherein the one or more side walls adjoin the planar top member at the upper edge. Preferably the cover also comprises a well formed in the top member, a ridge formed on the lower surface of the planar top member and surrounding the well, and one or more latching mechanisms on the lower edge of the one or more side walls. Preferably the ring structure of the device is sized to fit snugly in the bottom of the well of the base and of a height to contain sufficient cell culture media to enable culturing of cells in the well of the base. In preferred embodiments, the cover of the device is of similar overall shape as the base and fits snugly over the base, such that when the cover is placed on the base, the well of the cover fits into the well of the base and extends into the well of the base to rest against the ring when the ring is in the well of the base; the side walls of the cover fit alongside and enclose the side walls of the base; at least one latching mechanism in the lower edge of a cover side wall is aligned with a notch in the lower edge of a base side wall; and the ridge on the lower surface of the planar top member of the cover fits into the groove in the base.

Yet another embodiment of the present disclosure is a device comprising a base and a lid wherein the lid fits loosely over the base to allow air exchange and to prevent microbial contamination for cell growth, and wherein the lid is latchable to the base to form an air-tight and water-tight seal for transport of cultured cells in the same device, and wherein the device further comprises a support to hold a cell culture membrane in the base taut when the lid is latched to the base.

The ring structure of the device disclosed herein may have a height of from about 1 mm to about 4 mm, more preferably from about 1 mm to about 3 mm, or most preferably from about 1 mm to about 2 mm. Although the ring may be designed to hold any desired volume, in preferred embodiments the ring holds a volume of about 25 ml, about 20 ml, about 15 ml, about 10 ml, about 5 ml, about 4 ml, about 3 ml, about 2 ml or about 1 ml. In certain embodiments of the present disclosure, the device further comprises a deformable ring member sized and shaped to fit in the groove and to provide an air and liquid tight seal between the ridge of the cover and the base when the cover is latched to the base. The deformable ring member may be, for example, a silicon ring. In other embodiments of the present disclosure, the device further comprises a rim attached to the lower edge of the base side walls.

The devices disclosed herein may be in its overall shape circular, hexagonal, square, or triangular, as seen from above. The base and cover of the device may comprise materials such as polyethylene, polystyrene, polyethylene terephthalate, polycarbonate, polypropylene or combinations thereof. In preferred embodiments, at least a portion of the cover is transparent or translucent to enable a user to visualize the contents of the well of the base when the cover is assembled onto the base. Alternatively or in addition to being transparent or translucent, a portion of the planar top member of the cover may be frosted. Preferably, the device is sterilizable by gamma radiation or by autoclaving.

In still other embodiments of the present disclosure, the device further comprises cell culture media in the well of the base. The cell culture media may comprise, for example, a liquid or a gel. The disclosed devices preferably are designed to be used with a cell growth scaffold, i.e., cell culture support, such as a sponge or membrane that is placed in the well of the base plate and covered with cell culture medium. The cell culture support may be, for example, a membrane, a film, a foam, or a sponge, which may comprise biological, semi-synthetic or synthetic material. Examples of biological materials include but are not limited to human amniotic membrane, acellularised dermis, small intestinal submucosal membrane, or combination thereof. Examples of semi-synthetic materials include but are not limited to polylactic acid, polyglycolic acid, hyaluronic acid, or a combination thereof. Examples of synthetic materials include but are not limited to polyethylene, polypropylene, polybutylene, polystyrene, polycarbonate, polyethylene-terephthalate, or a combination thereof. The cell culture support may be transparent or translucent, or opaque. In certain embodiments, the cell culture support may be coated with one or more attachment factors such as, for example, laminin, fibronectin, collagen, fibrinogen, collagen IV, tenascin, bovine pituitary extract, epidermal growth factor, hepatocyte growth factor, keratinocyte growth factor, and hydrocortisone. The attachment factors may aid in cell attachment and cell spreading on the cell culture support.

Membranes made of biological materials like amniotic membrane or polymers may be self-adhering and tend to crinkle or wrinkle resulting in uneven distribution of cells on the membrane. The ring or gasket is designed to contact the perimeter of such a membrane and hold it against the bottom and/or sides of the walls of the well, thus holding the membrane taut during seeding of the cells when the device is used for culturing cells. Some membranes such as chitosan/polylactic acid (PLA) have a tendency to float in a culture dish, and the cells on the membrane surface may come directly in contact with the lid of the device. The provided ring ensures that the membranes are fixed to the bottom of the housing device and remain free of contact with the lid.

The ring provided with the disclosed devices thus protects a cell growth membrane during use, during the cell culturing period, when the cells are transported, and prior to transplantation, when the membranes/sponges are generally washed with buffered solutions to remove traces of transport media. The presence of the ring ensures that the membrane does not crinkle and damage the cells. Furthermore, it is generally advantageous in a clinical setting that the membranes are held taut so as to maintain a smooth surface enabling uniform cell attachment and growth.

The illustrated embodiment in the attached drawings having a roughly square lid component includes a planar top portion and outer walls extending downwardly from the planar top. The planar portion of the lid includes a well approximately centered in the top, which is configured to extend downwardly into the well or housing device of the base plate when the lid is placed on the base plate. The lid and base plate are designed such that, when a membrane and ring are in place in the housing device of the base plate, the well of the lid fits into the housing device and rests on the ring, thus holding the ring and membrane in place in the housing device. The lid also includes a continuous ridge concentric with and spaced outside the perimeter of the well. This ridge is designed to fit into the groove in the base plate when the lid is placed on the base. When the device is used for transport of a cell culture, a silicon gasket is placed in the groove and the ridge impinges on the silicon gasket effecting an airtight and liquid tight seal. In preferred embodiments, a snap is provided at the middle of each wall of the lid, each of which mates with a the notch in the wall of the base plate, securing the lid to the base plate.

BRIEF DESCRIPTION OF THE SEVERAL VIEWS OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

The following terms as used herein are understood to have their normal meanings as used in the art and are defined as follows:

Definitions:

The term "device" as used herein describes any container, apparatus, or vessel, which is intended for cell culture growth and transport.

Throughout the specification of the application, various terms are used such as "top," "bottom," "upper," "lower," "diagonal," and the like. These terms are words of convenience in order to distinguish between different elements. While such terms are provided to explain the cell culture device relative to positions in which the cell culture device may normally be used, such terms are not intended to be limiting as to how the different elements may be utilized.

The term "cells" is used herein, for the purposes of the specification and claims, to mean one or more of live cells, cells comprising cellular aggregates, or an organized structure or network of cells forming a tissue, as apparent to those skilled in the art.

The term "medium" or "media" is used herein, for the purposes of the specification and claims, to mean a liquid solution which is used to provide sufficient nutrients (e.g., vitamins, amino acids, essential nutrients, salts, and the like) and properties (e.g., osmolarity, buffering) to maintain living cells (or living cells in a tissue) and/or support their growth.

The term "membrane" is used herein, for the purpose of the specification and the claims, to mean sheet, film, foam, sponge, or the like. The membrane used in the practice of the present disclosure may either be of biological material, semi-synthetic material or synthetic material. Preferably, as used herein, these membranes can be easily detached or removed from the device. Examples of biological material as used herein include but are not limited to human amniotic membrane, acellularised dermis, small intestinal submucosal (SIS) membrane, and/or combinations thereof. The term "semi-synthetic material" includes but is not limited to poly-lactic acid (PLA), polyglycolic acid (PGA), hyaluronic acid, and/or combinations thereof.

Throughout this disclosure, unless the context dictates otherwise, the word "comprise" or variations such as "comprises" or "comprising" are understood to mean "includes, but is not limited to," such that other elements that are not explicitly mentioned may also be included. Further, unless the context dictates otherwise, use of the term "a" may mean a singular object or element, or it may mean a plurality, or one or more of such objects or elements.

The present disclosure relates to a cell culture device that can be used for, among other things, culturing cells, transporting cultured cells, and transplantation of cultured cells.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

The embodiment illustrated in the attached drawings is an example of a device with a roughly square configuration and with a circular housing device. The disclosure is not limited to this shape, however, as a device as disclosed herein can be of any appropriate shape or configuration, such as circular, hexagonal, triangular, or of any regular polygonal shape. The device is composed of moldable parts, and can be produced from a variety of medical grade materials, including but not limited to polyethylene, polystyrene, polyethylene terephthalate, polycarbonate and the like. The grade of the material is preferably clear, which enables a user to visualize the cells cultured on membranes held in the device, and allows inspection and photography of the cells throughout the growth period using a microscope.

Figure 1:
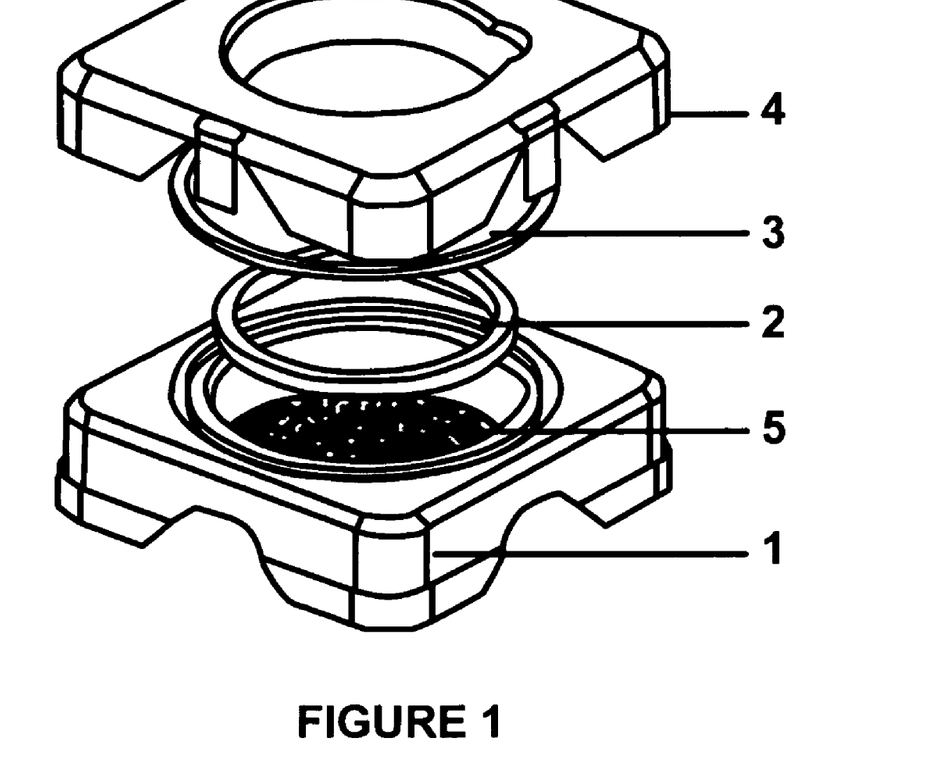
FIG. 1: Shows a perspective assembly view of the invention for culturing/transport of cells on membranes.

A device for culturing and/or transporting cells on membranes or sponges/gels is shown in an exploded view in FIG. 1. The two main body parts of the device are the base plate 1, and the top or lid 4. As can be seen from the drawing, the lid is shaped to fit over the base plate such that the side walls of the lid fit snugly to the outside surface of the side walls of the base. Also shown in FIG. 1 is a silicon ring or gasket 3, that forms a seal between the lid and the base and a ring 2, that holds the cell culture scaffold or membrane in the bottom of the housing device when the device is assembled for use. A membrane for cell culture and implantation 5 is also shown.

Figure 2:
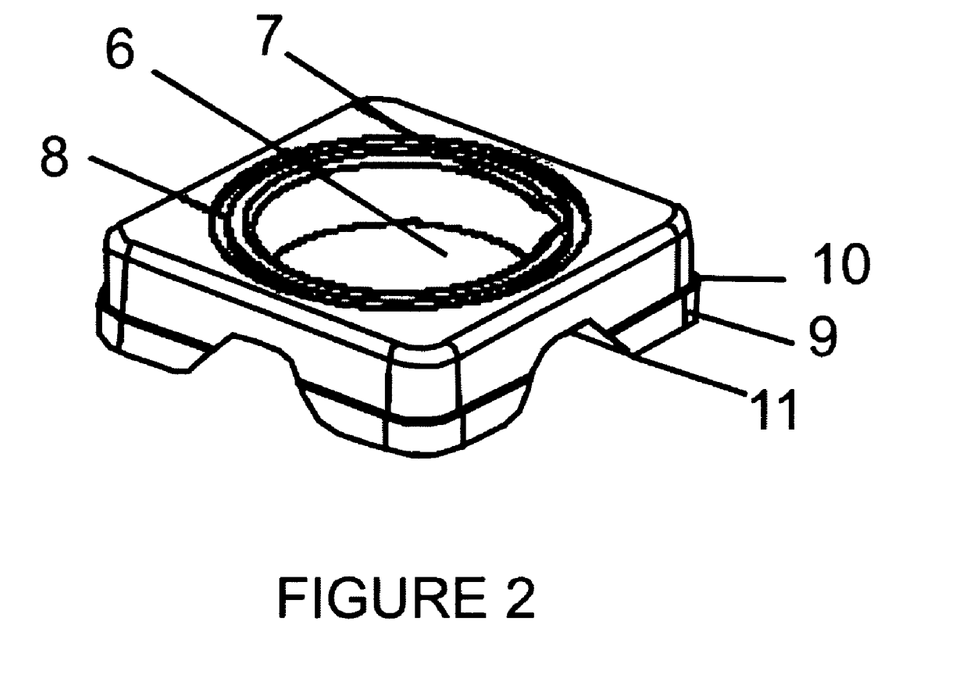
FIG. 2: Top view of the base.

A base plate of a preferred embodiment is shown in more detail in FIG. 2. As seen from a top perspective view, the base plate includes a planar top portion 18, and side walls 10 that terminate at the lower edge in a rim 9. Centered in the top portion 18, is a housing device 6 that extends into the interior of the base and holds the culture media and cell culture membrane during use. A groove 8 separates the housing device from the planar portion of the top. The bleb like region 7, is an area in the groove and top planar portion that provides a portal for a pipette device so the media can be easily changed by use of a pipette to drain or add the media to the housing device without disturbing the cells. The bleb portion can also be utilized for rinsing off the transport media from the final membrane or sponge before transplantation. The groove 8 also provides an exit for air trapped in the area above the ring, so that no air bubbles are present in the housing portion of the device during cell culture and transport. The groove 8 around the housing device also provides a track for the silicon gasket, to ensure airtight as well as leak proof conditions are maintained during transportation of the cells. The rim 9 skirts the outer wall 10 of the base plate and serves as a support during the opening and closing of the device. The notch 11 seen in the middle of each wall is for accepting the snaps 15 to firmly lock the lid to the base plate.

Figure 3:
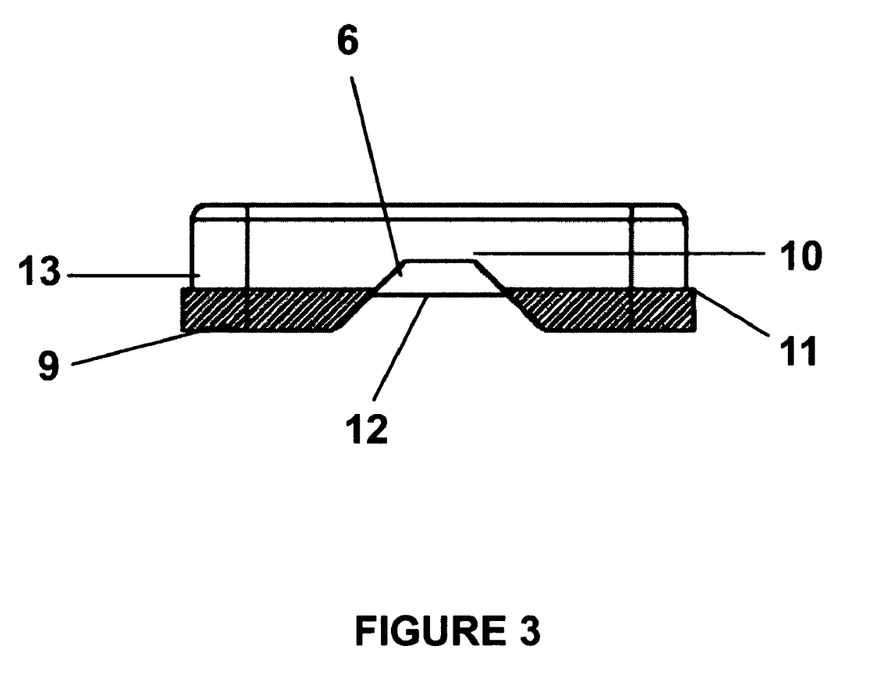
FIG. 3: Side view of the base plate.

A base plate of a preferred embodiment is illustrated in a side elevation view in FIG. 3. This illustration demonstrates that the bottom 12 of the housing device 6 is in a position approximately coplanar with the bottom 13 of the side walls 10, but does not extend as far as the bottom of the rim 9.

Figure 4:
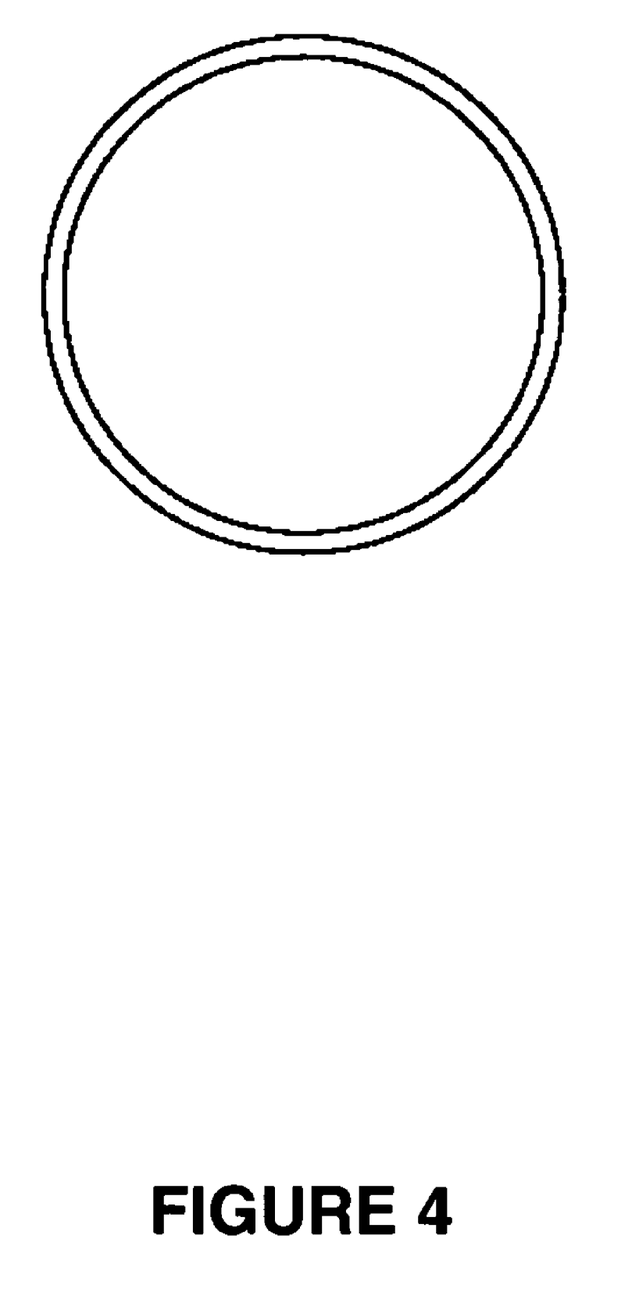
FIG. 4: View of the ring

FIG. 4 is a top view of a ring as used in a preferred embodiment. The height of the ring is such that on placing the ring inside the housing device and closing the lid, the base of the well located on the lid sits flush with the ring. The primary aim of the ring is to hold the membrane taut during cell culture and/or transport. The width of the ring is minimal to ensure larger area of cell coverage on the membrane/sponge.

Figure 5:
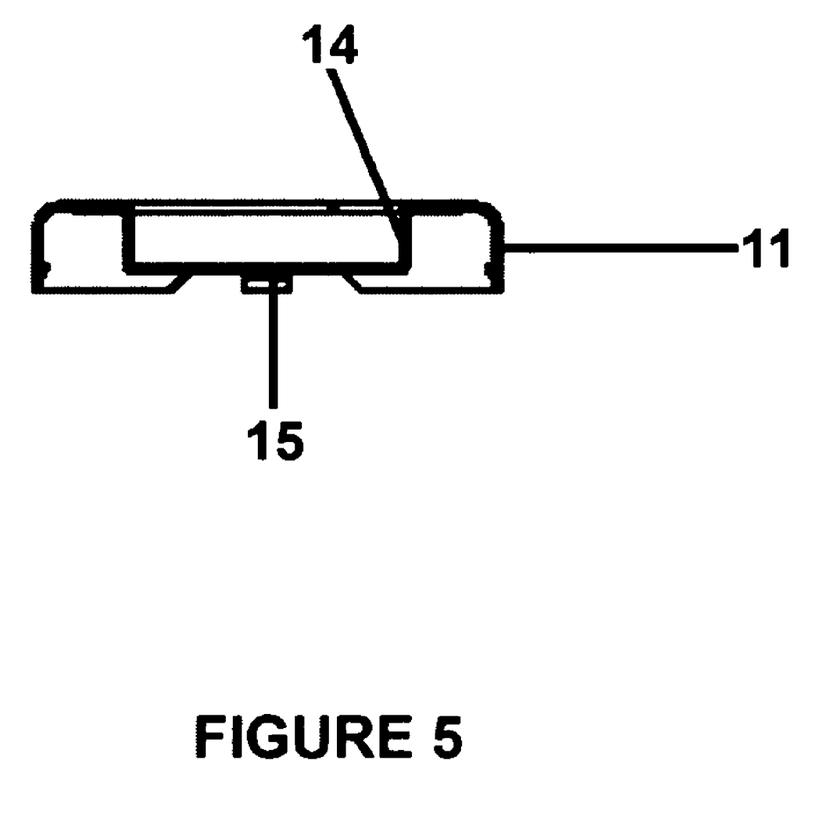
FIG. 5: Side view of the lid.
Figure 6:
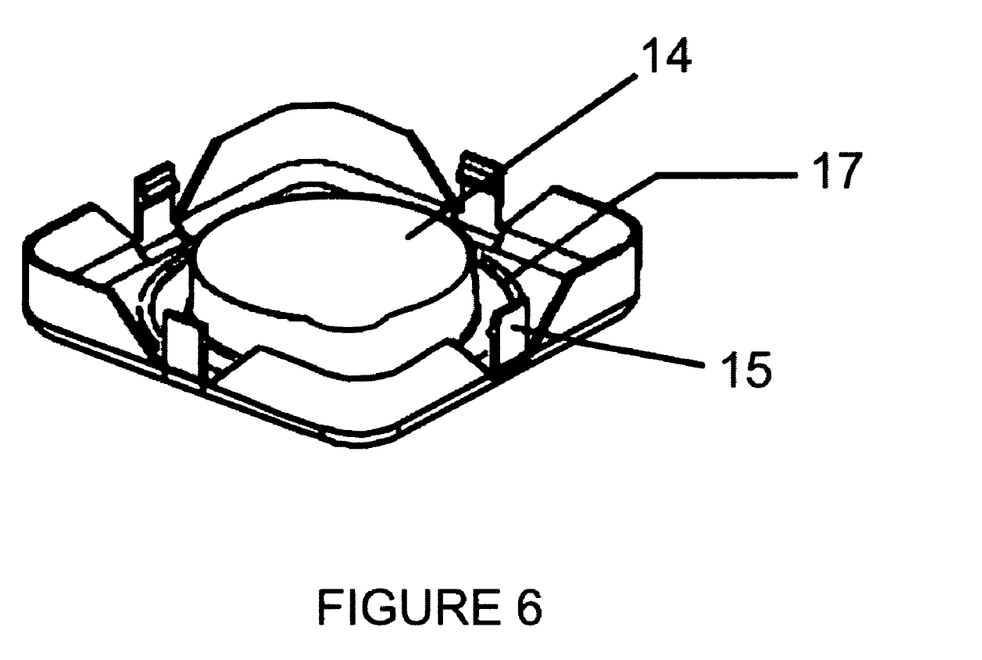
FIG. 6: Lower view of the lid.
Figure 7:
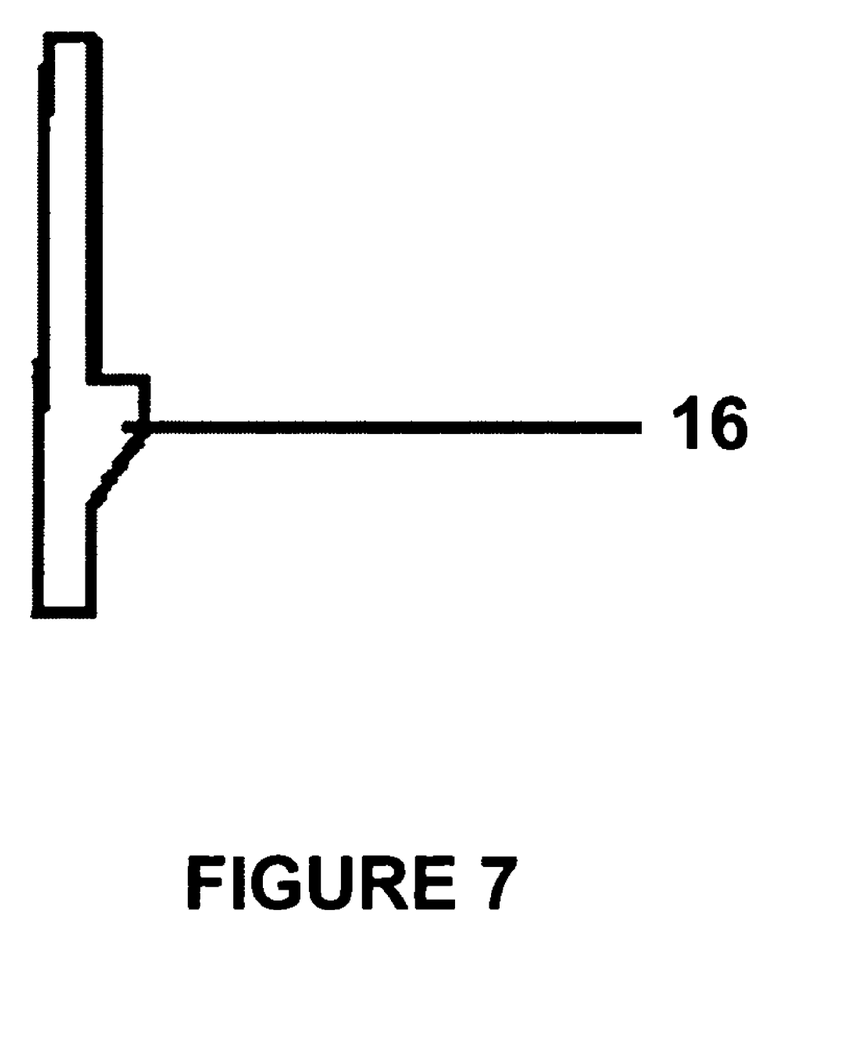
FIG. 7: Illustrated view of the notch

A lid of a preferred embodiment is shown in side elevational view in FIG. 5 and the lid is shown in a bottom perspective view in FIG. 6. The design of the lid is complementary to the matching base plate component so that the well 14 in the lid sits flush on the ring inside the housing device. Also shown in FIG. 6 is a ridge or protruding member 17 on the bottom of the planar top of the lid. The ridge is designed to fit in the groove 8 on the base and form a seal when a gasket is in the groove. In the middle of each wall of the lid is a snap 15, which is designed to lock firmly with the notch 11 provided in the base plate. A flange or angle 16 snaps below the side wall to lock the lid into place on the base. The number of snaps 15 or other locking mechanisms provided for each device can vary with the geometric design of the plate, for example a triangular device would preferably utilize three snaps.

In certain embodiments, the base and the lid can include orientation features that are used to orient the lid on the base to ensure that the lid fits correctly on the base. Such features can include, for example, a key and notch in the groove and ridge, or in the side walls of the housing device and well of the lid.

Figure 8:
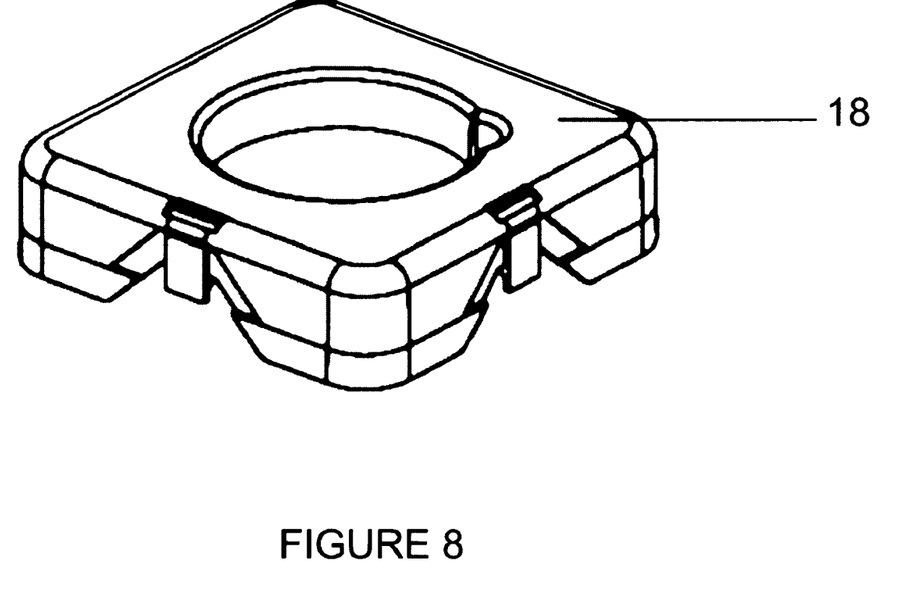
FIG. 8: Completely assembled view of the device.

An assembled device is shown in FIG. 8, in which the lid is locked onto the base by the snap mechanisms. In preferred embodiments, the planar top 18 can include a frosted area for the purpose of marking by the user.

The base, lid and ring can be molded using standard molding techniques (e.g., injection molding) generally known in the art. Sterilization of the devices can be done either by standard gamma radiation or by autoclaving. The devices can also be cleaned, sterilized and reused in some applications, for example in laboratory research.

For culturing cells using the present devices, a suspension of cells is added to the membrane/sponge supported by the ring inside the housing device. Alternatively, a suspension of cells in a gelling solution can be added to the culturing device. After the setting of the gel in the device, the cells can be cultured in the following manner.

The quantity of the media added to the device is such that it fills the space provided inside the ring. The lid is placed loosely over the base plate and the device is incubated under environmentally controlled conditions. For changing the media, the lid is lifted, the base plate gently angled and media is drained with the tip of a pipette introduced into the groove in the housing device. Fresh media can similarly be added to the housing device through the groove.

For transporting cells using the devices disclosed herein, cells cultured directly in the device or cultured in another device and placed in the device for transport can be shipped after adding appropriate transport media to the cells. The silicon gasket is placed inside the groove and the lid snapped tightly to the base to ensure that no air bubbles are entrapped. The devices of the present disclosure are preferably leak proof and air tight. The locked devices containing cells can be shipped under proper shipping conditions to a recipient.

After receiving the cells, the user breaks the snaps and drains the transport media (as mentioned above for media change). In preferred embodiments, the membrane/sponge is rinsed with buffered solution, the ring is lifted, and the underlying membrane/sponge can be transplanted directly to a patient.

The devices disclosed herein thus provide many advantages over conventional culture devices. Preferably, the devices are disposable and ready to use single devices for culturing and transport of cells. The devices can be sterilized by conventional autoclaving or gamma radiation techniques, and the media required for these devices is preferably less than 5 ml, as compared to 25 ml required by conventional cell culture flasks or dishes. In preferred embodiments, the lid of the device prevents microbial contamination, as well as provides aeration for optimum cell growth. A silicon gasket provided with the device preferably ensures an airtight seal and prevents leaking during transportation of the cells, thus maintaining viability. The cells can be incubated using this device in normal carbon-dioxide incubators. The risk of failure is minimized as the oxygen requirement for the maintenance of the cells is fulfilled. For example, when kept in the carbon-dioxide incubators without the silicon gasket, the device provides adequate aeration for optimal cell growth while providing gas exchange to take place. The devices are preferably composed of transparent or translucent material to enable inspection of the cells under microscope throughout the use of the device, and the simple and efficient design preferably occupies less space thus reducing the freight charges. Finally, there is no delay in transplantation as this device provides ready to use cells for transplantation after washing of the cells.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A cell culture device comprising:
   a base, wherein the base comprises:
      a planar top member and one or more side walls, each with an upper and lower edge, wherein the one or more sidewalls adjoin the planar top member at the upper edge;
      a well formed in the top member;
      a groove surrounding the well between the planar portion of the top member and the well; and
      one or more notches in the lower edge of the one or more side walls configured to receive a latching mechanism;
   a cover, comprising:
      a planar top member having an upper and a lower surface, and one or more side walls, each with an upper and lower edge, wherein the one or more side walls adjoin the planar top member at the upper edge;
      a well formed in the top member of said cover;
      a ridge formed on the lower surface of the planar top member and surrounding the well; and
      one or more latching mechanisms on the lower edge of the one or more side walls of said cover; and
   a ring structure sized to fit snugly in the bottom of the well of the base and of a height to contain sufficient cell culture media to enable culturing of cells in the well of the base;
   wherein the cover is of similar overall shape as the base and fits snugly over the base, such that when the cover is placed on the base;

the well of the cover fits into the well of the base and extends into the well of the base to rest against the ring when the ring is in the well of the base;

the side walls of the cover fit alongside and enclose the side walls of the base;

at least one latching mechanism in the lower edge of a cover side wall is aligned with a notch in the lower edge of a base side wall; and the ridge on the lower surface of the planar top member of the cover fits into the groove in the base.

2. The device of claim 1, further comprising a deformable ring member sized and shaped to fit in the groove and to provide an air and liquid tight seal between the ridge of the cover and the base when the cover is latched to the base.

3. The device of claim 2, wherein the deformable ring member is a silicon ring.

4. The device of claim 1, further comprising a rim attached to the lower edge of the base side walls.

5. The device of claim 1, wherein the overall shape of the device as seen from above is circular, hexagonal, square, or triangular.

6. The device of claim 1, wherein the base and cover comprise polyethylene, polystyrene, polyethylene terephthalate, polycarbonate, polypropylene or combinations thereof.

7. The device of claim 1, wherein at least a portion of the cover is transparent or transluscent to enable a user to visualize the contents of the well of the base when the cover is assembled onto the base.

8. The device of claim 1, wherein a portion of the planar top member of the cover is frosted.

9. The device of claim 1, wherein the device is sterilizable by gamma radiation or by autoclaving.

10. The device of claim 1, wherein the height of the ring is from about 1 mm to about 4 mm.

11. The device of claim 1, wherein the height of the ring is from about 1 mm to about 2 mm.

12. The device of claim 1, wherein the ring holds a volume of about 5 ml.

13. The device of claim 1, further comprising cell culture media in the well of the base.

14. The device of claim 13, wherein the cell culture media comprises a liquid or a gel.

15. The device of claim 1, further comprising a cell culture support in the well of the base.

16. The device of claim 15, wherein the cell culture support is a membrane, a film, a foam, or a sponge.

17. The device of claim 16, wherein the cell culture support is a membrane comprising biological, semi-synthetic or synthetic material.

18. The device of claim 17, wherein the biological material is human amniotic membrane, acellularised dermis, small intestinal submucosal membrane or combination thereof.

19. The device of claim 17, wherein the semi-synthetic material comprises polylactic acid, polyglycolic acid, hyaluronic acid, or a combination thereof.

20. The device of claim 17, wherein the synthetic material is polyethylene, polypropylene, polybutylene, polystyrene, polycarbonate, polyethylene-terephthalate, or a combination thereof.

21. The device of claim 17, wherein the membrane is transparent or transluscent.

22. The device of claim 17, wherein the membrane is opaque.

23. The device of claim 22, wherein the membrane is coated with one or more attachment factors selected from the group consisting of laminin, fibronectin, collagen, fibrinogen, collagen IV, tenascin; bovine pituitary extract, epidermal growth factor, hepatocyte growth factor, keratinocyte growth factor, and hydrocortisone.

* * * * *